US010773041B2

(12) United States Patent
Jeffrey et al.

(10) Patent No.: US 10,773,041 B2
(45) Date of Patent: Sep. 15, 2020

(54) MEDICO-SURGICAL TUBE ASSEMBLIES AND FLANGE ASSEMBLIES

(71) Applicant: SMITHS MEDICAL INTERNATIONAL LIMITED, Ashford (GB)

(72) Inventors: Andrew Thomas Jeffrey, Hythe (GB); Christopher John Woosnam, Great Sutton (GB)

(73) Assignee: Smiths Medical International Limited, Kent (GB)

( * ) Notice: Subject to any disclaimer, the term of this patent is extended or adjusted under 35 U.S.C. 154(b) by 258 days.

(21) Appl. No.: 16/071,561

(22) PCT Filed: Jan. 18, 2017

(86) PCT No.: PCT/GB2017/000005
§ 371 (c)(1),
(2) Date: Jul. 20, 2018

(87) PCT Pub. No.: WO2017/129935
PCT Pub. Date: Aug. 3, 2017

(65) Prior Publication Data
US 2019/0151588 A1    May 23, 2019

(30) Foreign Application Priority Data
Jan. 28, 2016 (GB) .................................. 1601583.6

(51) Int. Cl.
A61M 16/04    (2006.01)
A61M 25/02    (2006.01)

(52) U.S. Cl.
CPC .... *A61M 16/0497* (2013.01); *A61M 16/0465* (2013.01); *A61M 16/0488* (2013.01); *A61M 2025/024* (2013.01)

(58) Field of Classification Search
CPC .............. A61M 16/04; A61M 16/0427; A61M 16/0463; A61M 16/0465; A61M 16/0472;
(Continued)

(56) References Cited

U.S. PATENT DOCUMENTS 2,820,457 A    1/1958 Phillips
4,895,570 A *  1/1990 Larkin ............... A61M 39/1011
                                                        604/411
(Continued)

FOREIGN PATENT DOCUMENTS

EP    2873432 A1    5/2015
WO    2008/083286 A1    7/2008

OTHER PUBLICATIONS

PCT International Search Report and Written Opinion, PCT/GB2017/000005, EPO dated Mar. 22, 2017.

*Primary Examiner* — Joseph D. Boecker
(74) *Attorney, Agent, or Firm* — Louis Woo

(57) ABSTRACT

A tracheostomy tube (1) has an adjustable flange (2) that can be slid along the tube and locked in the desired position. The flange has a one-piece resilient nut (40) that is threaded on a tubular projection (30) on the flange. The nut has an integral inner sleeve (44) divided into separate fingers (48) the outside of which are engaged by the inside of the tubular projection. The flange is locked in position by screwing the nut onto the projection so that the fingers that are forced inwardly to engage the outside of the tube.

9 Claims, 4 Drawing Sheets

(58) Field of Classification Search
CPC .......... A61M 16/0488; A61M 16/0493; A61M 16/0497; A61M 2025/0006; A61M 2025/024; A61M 39/1011; A61M 2039/1016; A61M 2039/1033; A61M 2039/1038
See application file for complete search history.

(56) References Cited

U.S. PATENT DOCUMENTS

| | | | |
|---|---|---|---|
| 5,020,534 A | 6/1991 | Pell et al. | |
| 5,251,616 A | 10/1993 | Desch | |
| 10,603,455 B2 * | 3/2020 | Jeffrey | A61M 16/0465 |
| 2003/0193190 A1 * | 10/2003 | Werth | F16L 33/225 |
| | | | 285/243 |
| 2006/0033334 A1 * | 2/2006 | Weber | A61M 39/10 |
| | | | 285/390 |
| 2009/0264003 A1 * | 10/2009 | Hertzler | H01R 13/5219 |
| | | | 439/299 |
| 2012/0216803 A1 | 8/2012 | Trodler | |

* cited by examiner

MEDICO-SURGICAL TUBE ASSEMBLIES AND FLANGE ASSEMBLIES

This invention relates to medico-surgical tube assemblies of the kind including a tube and a flange assembly movable along the tube, the flange assembly including a flange and a locking arrangement having a tubular projection extending from the flange and a locking nut threaded on the tubular projection.

Medico-surgical tubes, such as tracheostomy tubes, are commonly provided with a flange to secure the tube to the patient's body. In the case of a tracheostomy tube, the flange is positioned close to the surface of the neck where the tube enters the tracheostomy, a tape being threaded through openings in the flange and fastened around the neck. For most patients, a comfortable fit can be achieved using one of a range of several different size tubes, each having a flange mounted at a fixed location along the tube suitable for patients having an average anatomy. There are, however, some situations where a fixed flange is not suitable, such as, for example, in obese patients where tissue between the neck surface and the trachea is very thick. In these situations, it is preferable for the flange to be movable along the tube to the ideal position and to be lockable in that position. Tubes with adjustable flanges are described in, for example, U.S. Pat. Nos. 5,026,352, 4,249,529, 4,449,527, 4,498,903, 4,530,354, 4,530,354, 4,649,913, 4,683,882, 4,774,944, WO80/02645, WO84/03217, U.S. Pat. No. 4,278,081, WO06/087513 and WO16/116721. U.S. Pat. No. 8,104,476 describes a tube with an adjustable flange having two halves that clamped about the outside of a tube when a lever is folded flat. Rusch sells a tracheostomy tube "Tracflex Plus Set" with a flange that is locked by twisting a nut. It is important to achieve a secure fastening of the flange to the tube even when this is wet and slippery. Various previous arrangements have required multiple components to lock the flange in position, leading to additional manufacturing and assembly costs and the added risk of components separating and entering the surgical site.

It is an object of the present invention to provide an alternative medico-surgical tube assembly and flange assembly for a medico-surgical tube assembly.

According to one aspect of the present invention there is provided a medico-surgical tube assembly of the above-specified kind, characterised in that the locking nut is of a one-piece deformable, compliant material including an outer collar having a screw thread on its inner surface extending axially along the outside of the outer collar, that the tubular projection has a screw thread on its outer surface engaged by the thread on the outer collar of the nut, that the locking nut also includes an integral inner sleeve extending coaxially within both the outer collar and the tubular projection, that the inner surface of the sleeve embraces and contacts the outer surface of the tube, and that the inner sleeve is divided into a plurality of separate fingers the outer surface of which is contacted by the tubular projection on the flange, the fingers and tubular projection being arranged such that the ends of the fingers are urged inwardly by engagement with the tubular projection into closer contact with the tube as the locking nut is screwed onto the tubular projection.

The tubular projection projecting from the flange and the fingers of the inner sleeve are preferably formed with cooperating inclined surfaces. The inclined surfaces may be convex curved surfaces. The rear end of the tubular projection may be formed on its inner surface with a surface formation adapted to engage a surface formation on the inner surface at the forward end of the inner sleeve so as to prevent removal of the locking nut from the flange assembly when in position on the tube. The spacing between the fingers of the inner sleeve is preferably selected such that the fingers engage one another towards their ends during tightening of the locking nut such as to limit inward displacement of the fingers and thereby limit the force applied to the outer surface of the tube. The locking nut may be of neoprene. The assembly may be a tracheostomy assembly and the tube may be a tracheostomy tube.

According to another aspect of the present invention there is provided flange assembly for a tube assembly according to the above one aspect of the present invention.

According to a further aspect of the present invention there is provided a flange assembly for a medico-surgical tube assembly including a flange and a locking arrangement having a tubular projection extending from the flange and a locking nut threaded on the tubular projection, characterised in that the locking nut is of a one-piece deformable, compliant material including an outer collar having a screw thread on its inner surface extending axially along the outside of the outer collar, that the tubular projection has a screw thread on its outer surface engaged by the thread on the outer collar of the nut, that the locking nut also includes an integral inner sleeve extending coaxially within both the outer collar and the tubular projection, that the inner surface of the sleeve is arranged to embrace and contact the outer surface of a tube, and that the inner sleeve is divided into a plurality of separate fingers the outer surface of which is contacted by the tubular projection on the flange, the fingers and tubular projection being arranged such that the ends of the fingers are urged inwardly by engagement with the tubular projection into closer contact with the tube as the locking nut is screwed onto the tubular projection.

A tracheostomy tube assembly including a flange assembly, both according to the present invention will now be described, by way of example, with reference to the accompanying drawing, in which.

Figure 1:
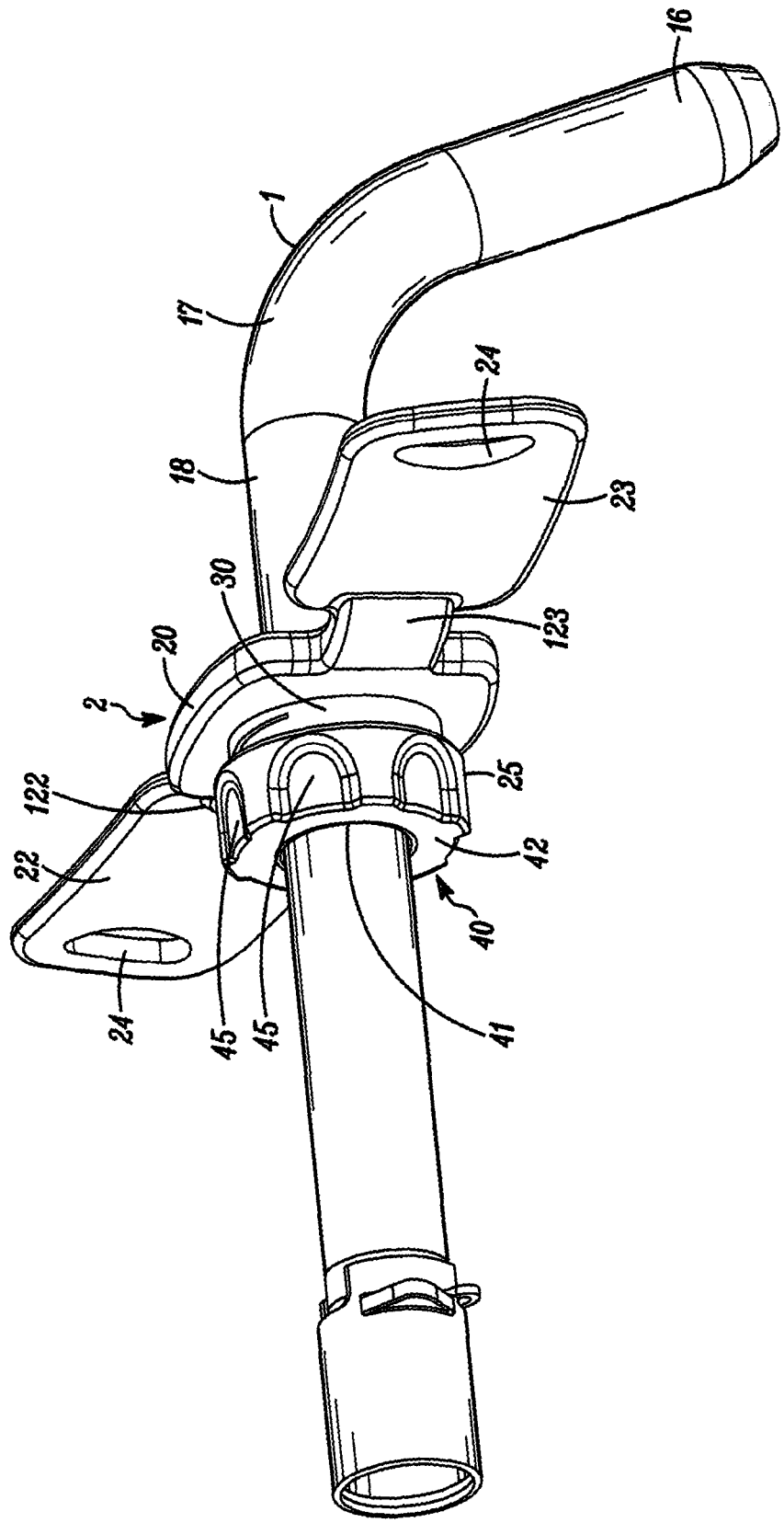
FIG. 1 is a perspective view of the tube assembly where the flange is unlocked.

With reference first to FIG. 1, the tube assembly comprises a tube 1 and a flange assembly 2 with a locking arrangement 25, the flange assembly being movable along the tube and lockable at different locations along its length.

The tube 1 is made of a conventional, bendable plastics material, such as PVC, polyurethane or silicone, is hollow with a circular section and has a smooth inner surface. The outer surface may also be smooth or it could be textured to improve the grip of the flange assembly 2. The tube 1 may have a shaft reinforced with a helical wire or similar member. The tube 1 is illustrated as not having any sealing cuff but it will be appreciated that the invention could be applied to a tracheostomy tube with an inflatable or other form of conventional sealing cuff. Similarly, the tube could have other conventional features, such as provision for suctioning above a cuff, fenestrations to enable speech and the like. The shaft of the tube 1 comprises a straight patient end region 16, a curved intermediate region 17 and a straight machine end region 18 extending at substantially 120° to the patient end region. Alternative shape shafts are possible, such as shafts that are curved continuously along their length or shafts that have a natural straight shape but are highly flexible so that they can conform readily to the shape of the anatomy.

Figure 2:
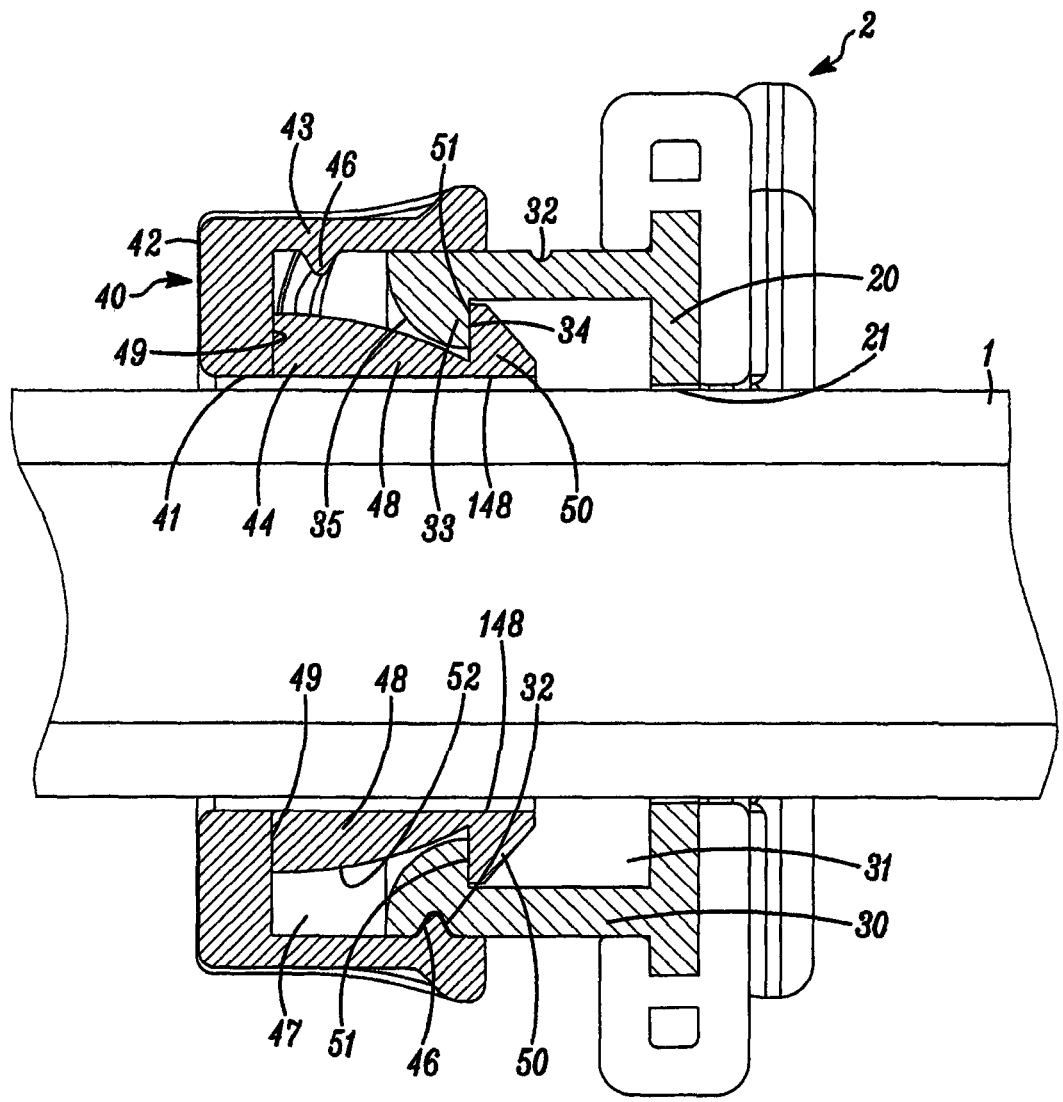
FIG. 2 is an enlarged cross-sectional side elevation of the flange assembly in the unlocked state.

With reference now also to FIG. 2, the flange assembly 2 has a rectangular central plate 20 with a central circular aperture 21 the diameter of which is such that the tube 1 is a close sliding fit within it. Two wings 22 and 23 extend from the central plate 20 on opposite sides. The two wings 22 and 23 are generally rectangular, being curved slightly along their length and are each formed with a lateral slot 24 towards their free end by which a tape, strap or the like can be secured to the wing. The two wings 22 and 23 are attached with the central plate 20 by respective flexure sections or webs 122 and 123 formed integrally with the plate and the wings. The webs 122 and 123 have a reduced width compared with the plate 20 and wings 22 and 23 to allow them to flex when the wings are pulled forwardly. This allows the wings 22 and 23 to hinge when they are pulled forwardly after positioning, for access, observation or cleaning of the region under the flange. The reduced width of the webs 122 and 123 also allows some rotational movement between the wings and the central plate, and hence the tube. This helps reduce the torque applied to the patient. The central plate 20, wings 22 and 23 and webs 122 and 123 together provide the flange of the flange assembly 2. The flange assembly 2 is arranged such that the forward, patient side of the wings 22 and 23 is set forwardly relative to the forward side of the central plate 20 by 1-2 mm so as to reduce pressure on the stoma site. The wings 22 and 23 are further designed to be relative large in area so as to help reduce pressure on any one part of the neck anatomy, which may help reduce pressure sores. The large size of the wings 22 and 23 reduces the risk of the flange becoming lost in the skin folds present in patients with a larger neck mass.

FIGS. 1 and 2 show the locking arrangement 25 of the flange assembly 2 in a released or unlocked state. The locking arrangement 25 includes a tubular projection or collar 30 of circular section formed integrally with the central plate 20 of the flange, of a relatively rigid material. The projection 30 projects rearwardly, that is, away from the patient and has an inner diameter larger than that of the central aperture 21 so that it is spaced from the outside of the tube 1 by an annular gap 31. Along its outside, the projection 30 is formed with a screw thread 32 indented in its outer surface. The inside of the projection 30 is smooth except for an inwardly-projecting annular lip or catch 33 providing a surface formation in the form of a flat forwardly-facing engagement surface 34. The catch 33 is also shaped to form a curved entrance surface 35 into the interior of the projection 30.

Figure 3:
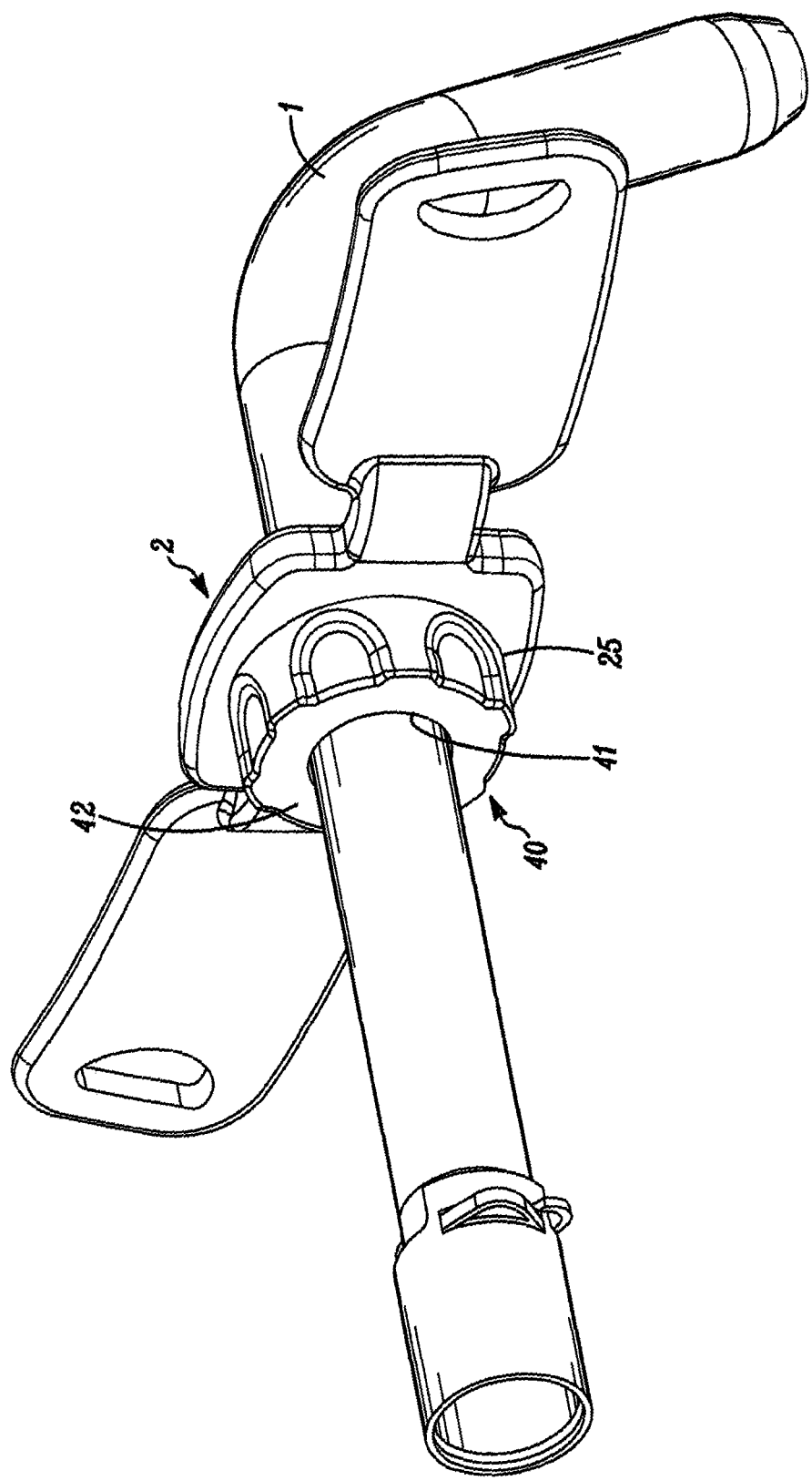
FIG. 3 is a perspective view of the tube assembly where the flange is locked in position.

The other part of the locking arrangement 25 is provided by an integral, one-piece moulded compression nut 40. The nut 40 is moulded from a relatively compliant, resilient material, such as neoprene that is softer than the projection 30 on the flange assembly 2. The nut 40 has a central passage 41 along its length through which the tube 1 extends. At its rear end (away from the patient) the nut 40 has a closed end face 42 from which project an outer collar 43 and an inner sleeve 44. The outer collar 43 is moulded on its outer surface with knurls 45 or other surface formations to improve grip on the nut. The inner diameter of the outer collar 43 is slightly less than the outer diameter of the flange projection 30 and its inner surface is moulded with a projecting screw thread 46 that engages the screw thread 32 on the outside of the flange projection. In this way, gripping the outside of the nut 40 and twisting it causes it to be drawn forwardly along the flange projection 30 from the rear position shown in FIGS. 1 and 2 to the forward position shown in FIGS. 3 and 4. The inner sleeve 44 of the nut 40 extends coaxially forwardly within the outer collar 43 and is spaced from the inside of the outer collar by an annular space 47. The inner surface of the inner sleeve 44 provides the central passage 41 through which the tube 1 extends. The inner sleeve 44 is divided into four separate fingers 48 by four slots 49 extending from close to the rear end face 42 to the forward end of the sleeve. The forward end of the inner sleeve 44 projects a short distance beyond the forward end of the outer collar 43 and each of the fingers 48 is formed on their inner surface with an inwardly-projecting catch 50 having a rearwardly-facing, radially-extending flat surface 51 shaped to abut the engagement surface 34 around the catch 33 on the flange collar 30 when the nut 40 is at its rearmost position. The engagement of the catches 33 and 50 limits how far the nut 40 can be unscrewed and prevents the nut being removed from the flange assembly 2 while the nut is on the tube 1. The radial thickness of the fingers 48 increases rearwardly giving the outer surface 52 of the fingers 48 a convex taper along their length.

Figure 4:
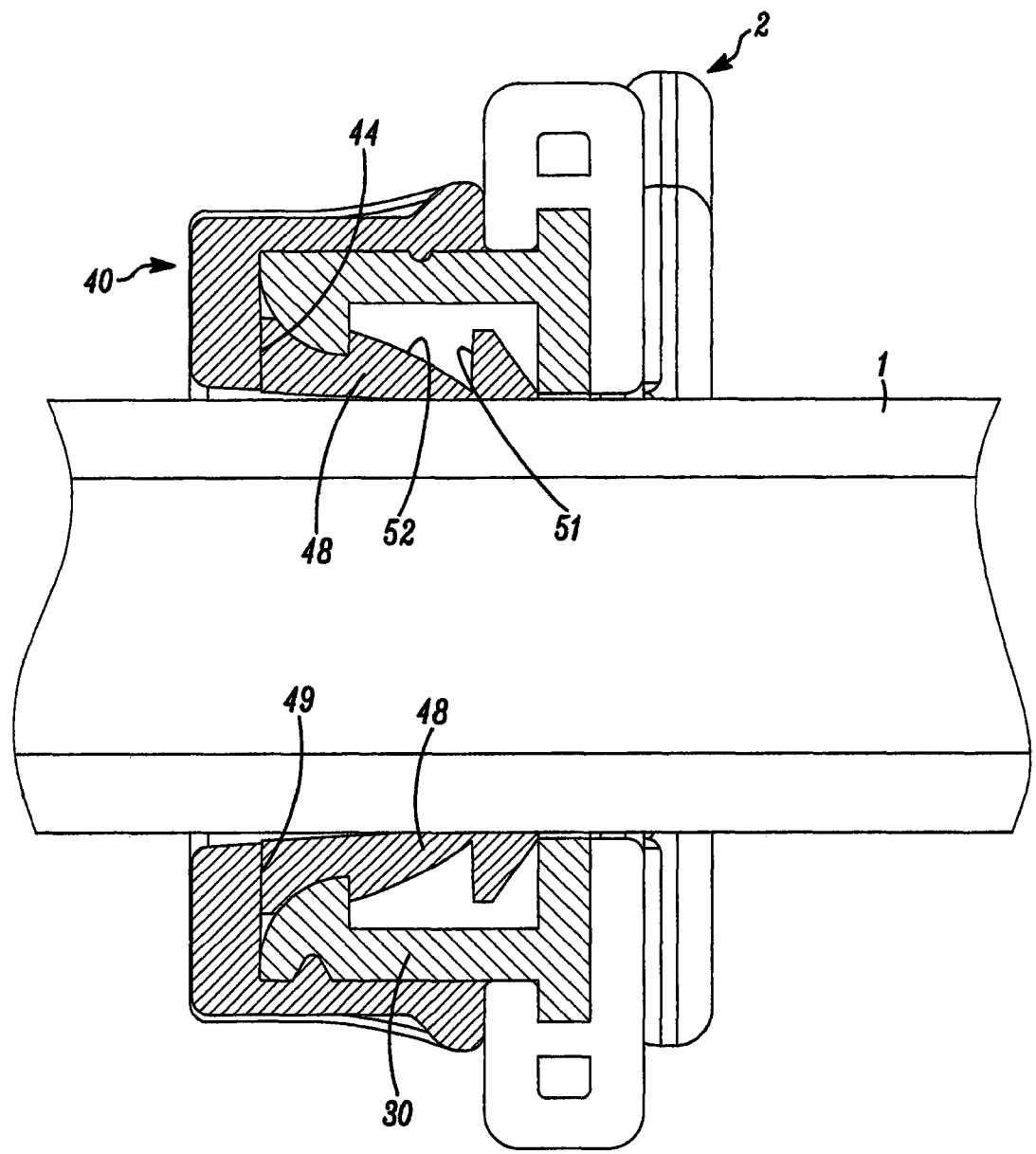
FIG. 4 is an enlarged cross-sectional side elevation of the flange in a locked state.

When the nut 40 is in its outermost or rearmost, unlocked position shown in FIGS. 1 and 2, the inner tip of the catch 33 engages the outer surface of the fingers 48 just to the rear of the catches 50 on the fingers, where the fingers are thinnest. In this position the inner surface 148 of the fingers 48 exerts little or no force on the outside of the tube 1 so that the been positioned at the desired location along the tube 1 it is locked in position by twisting the nut 40 clockwise as far as it can so that the nut is screwed forwards from the unlocked position shown in FIGS. 1 and 2 to the locked position shown in FIGS. 3 and 4. As can be seen in FIG. 4, in this locked position the catch 33 on the flange projection 30 bears against the rear, thickest part of the inner sleeve 44 and its fingers 48 so that an inwardly-directed force is thereby applied to the fingers, forcing them against the outer surface of the tube 1 and reducing the width of the slots 49 between the fingers at their outer ends. In order to prevent excessive pressure being applied to the outer surface of the tube 1, which could cause deformation of the outer surface and permanent indentations, it is desirable to limit the force that can be applied. In the present arrangement this is achieved by appropriately selecting the width of the slots 49 between the fingers 48 such that the outermost, forward end of the slots close completely and the tips of adjacent fingers contact one another when the maximum desired clamping pressure is achieved. In this way, no further clamping force can be achieved without applying a considerably greater twisting force to the nut 40, thereby making it apparent that the flange assembly 2 is fully locked in position.

The present invention enables a single component to provide both the compressive, frictional engagement with the outside of the tube and the manually-engageable surface by which the locking arrangement is locked and unlocked. In this way, the same material can be used to provide the desired compliance both to the part that grips the tube and the part that is gripped by hand. It also enables the projection on which the nut is threaded to be of a stiffer material if need be to provide increased dimensional stability. The invention can also be used to ensure that excessively large gripping forces, of the kind that might damage or deform the tube, are not applied.

The invention is not confined to tracheostomy tubes but could be used with other medico-surgical tubes having a flange for supporting the tube where it emerges from the body.

The invention claimed is:

1. A medico-surgical tube assembly including a tube and a flange assembly movable along the tube, the flange assembly including a flange and a locking arrangement having a tubular projection extending from the flange and a locking nut threaded on the tubular projection, characterised in that the locking nut is of a one-piece deformable, compliant material including an outer collar having a screw thread on its inner surface extending axially along an inside of the outer collar, that the tubular projection has a screw thread on its outer surface engaged by the thread on the outer collar of the nut, that the locking nut also includes an integral inner sleeve extending coaxially within both the outer collar and the tubular projection, that the inner surface of the sleeve embraces and contacts the outer surface of the tube, and that the inner sleeve is divided into a plurality of separate fingers the outer surface of which is contacted by the tubular projection on the flange, the fingers and tubular projection being arranged such that the ends of the fingers are urged inwardly by engagement with the tubular projection into closer contact with the tube as the locking nut is screwed onto the tubular projection.

2. An assembly according to claim 1, characterised in that the tubular projection projecting from the flange and the fingers of the inner sleeve are formed with cooperating inclined surfaces.

3. An assembly according to claim 2, characterised in that the inclined surfaces are convex curved surfaces.

4. An assembly according to claim 1, characterised in that a rear end of the tubular projection is formed on its inner surface with a surface formation adapted to engage a surface formation on the inner surface at a forward end of the inner sleeve so as to prevent removal of the locking nut from the flange assembly when in position on the tube.

5. An assembly according to claim 1, characterised in that the spacing between the fingers of the inner sleeve is selected such that the fingers engage one another towards their ends during tightening of the locking nut such as to limit inward displacement of the fingers and thereby limit the force applied to the outer surface of the tube.

6. An assembly according to claim 1, characterised in that the locking nut is of neoprene.

7. An assembly according to claim 1, characterised in that assembly is a tracheostomy assembly, and that the tube is a tracheostomy tube.

8. A flange assembly for a tube assembly movable along a medico-surgical tube, the flange assembly including a flange and a locking arrangement having a tubular projection extending from the flange and a locking nut threaded on the tubular projection, characterised in that the locking nut is of a one-piece deformable, compliant material including an outer collar having a screw thread on its inner surface extending axially along an outside of the outer collar, that the tubular projection has a screw thread on its outer surface engaged by the thread on the outer collar of the nut, that the locking nut also includes an integral inner sleeve extending coaxially within both the outer collar and the tubular projection, that the inner surface of the sleeve embraces and contacts the outer surface of the tube, and that the inner sleeve is divided into a plurality of separate fingers the outer surface of which is contacted by the tubular projection on the flange, the fingers and tubular projection being arranged such that ends of the fingers are urged inwardly by engagement with the tubular projection into closer contact with the tube as the locking nut is screwed onto the tubular projection.

9. A flange assembly for a medico-surgical tube assembly including a flange and a locking arrangement having a tubular projection extending from the flange and a locking nut threaded on the tubular projection, characterised in that the locking nut is of a one-piece deformable, compliant material including an outer collar having a screw thread on its inner surface extending axially along a outside of the outer collar, that the tubular projection has a screw thread on its outer surface engaged by the thread on the outer collar of the nut, that the locking nut also includes an integral inner sleeve extending coaxially within both the outer collar and the tubular projection, that the inner surface of the sleeve is arranged to embrace and contact the outer surface of a tube, and that the inner sleeve is divided into a plurality of separate fingers the outer surface of which is contacted by the tubular projection on the flange, the fingers and tubular projection being arranged such that a ends of the fingers are urged inwardly by engagement with the tubular projection into closer contact with the tube as the locking nut is screwed onto the tubular projection.

* * * * *